United States Patent [19]

Yamahira et al.

[11] 4,244,943
[45] Jan. 13, 1981

[54] METHOD FOR PREPARING UROKINASE INJECTION

[75] Inventors: Yoshiya Yamahira, Ibaraki; Keiji Fujioka, Amagasaki; Yoshiko Okuzawa, Nishinomiya; Seiko Miura; Shigeji Sato, both of Ibaraki, all of Japan

[73] Assignee: Sumitomo Chemical Company, Limited, Osaka, Japan

[21] Appl. No.: 37,280

[22] Filed: May 9, 1979

[30] Foreign Application Priority Data

May 12, 1978 [JP] Japan .................................. 53/56826

[51] Int. Cl.³ ..................... A61K 37/48; A61K 37/00; C12N 9/96; C12N 9/72
[52] U.S. Cl. ...................................... 424/94; 424/177; 435/188; 435/215

[58] Field of Search .................. 424/94, 177; 435/215, 435/188

[56] References Cited

PUBLICATIONS

Miyata et al., Chem. Abst., vol. 88, (1978), p. 18304d.
Yukari et al., Chem. Abst., vol. 82, (1975), p. 27955v.

*Primary Examiner*—Delbert R. Phillips
*Attorney, Agent, or Firm*—Stevens, Davis, Miller & Mosher

[57] ABSTRACT

A method for preparing a stable urokinase injection by the liophilization of urokinase which comprises liophilizing an aqueous solution containing urokinase, human serum albumin and one or more amino acid compounds selected from polar amino acids and salt thereof. The urokinase injection obtained according to this method is excellent in the storing stability as compared with conventional urokinase preparations for injection.

12 Claims, No Drawings

METHOD FOR PREPARING UROKINASE INJECTION

The present invention relates to a urokinase injection and a method of preparing the same. More particularly, the invention relates to an inproved urokinase preparation for injection and a method for preparing said urokinase preparation which comprises lyophilizing an aqueous solution containing urokinase, human serum albumin (hereinafter referred to as HSA), and one or more polar amino acids or salts thereof.

Urokinase is now widely used as a fibrinolytic agent in the therapy of thrombotic diseases. For this purpose, a highly purified urokinase is obtained, for example, by isolation from fresh human urine and succeeding purification.

Since urokinase is very unstable in aqueous solutions, an urokinase preparation is generally prepared by lyophilizing an aqueous solution of urokinase in the presence of mannit, albumin or the like.

However, the stability of the urokinase preparations obtained as above can hardly be called sufficient and the biological potency of the urokinase preparation noticeably decreases during storage.

The present inventors now have found, as a result of a study, that a combination of HSA with a polar amino acid has a specific stabilizing effect on urokinase, and a highly stable urokinase preparation can be obtained by lyophilizing an aqueous solution of urokinase in the presence of HSA and a polar amino acid. It is also found that the combination of the present invention synergically improves the stability of urokinase preparations.

Thus, the present invention provides a novel method of stabilizing urokinase by use of a stabilizing agent comprising a combination of HSA and a polar amino acid or a salt thereof.

An object of this invention is to provide a more stable urokinase injection which is expected to be more efficacious compared with conventional urokinase preparations for injection.

Another object of this invention is to provide a method for preparing said more stable urokinase injection.

Other objects and advantages of this invention will become apparent from the following description.

The method for preparing a urokinase injection according to this invention is that in making urokinase into an injection, HSA and a polar amino acid or a salt thereof are added to an aqueous urokinase solution prior to lyophilization and then the resulting solution is lyophilized. Such a combination has a specific effect which cannot be observed with combinations of any other substances. The specific and synergic stabilizing effect of the combination according to this invention is described below in detail.

The stabilization effect of the combination stabilizer of this invention can be specifically observed only in the combination of HSA and a polar amino acid or a salt thereof, and there can not be observed such a remarkable stabilizing effect as above even in the combination of HSA with other optional non-polar amino acid, such as for example, cystein, leucine, methionine and the like.

The "polar amino acids" as herein referred to are based on the classification described in "Physics of Enzyme" (written by M.V. Volkenshtein, translated into Japanese by Toyokazu Tanaka, and published by Misuzu Shobô Co., 1972) and include those amino acids which are more hydrophilic in overall properties such as Arg, Asp, Asp(NH$_2$), Glu, Glu(NH$_2$), His, Lys, Ser and Thr. The "nonpolar amino acids" as herein referred to are also based on the classification according to the same author and are those amino acids which are more hydrophobic in overall properties.

The stabilizing effect of the combination according to this invention can be exhibited with pretty small amounts of amino acid compounds if HSA is present in sufficiently large amounts or, conversely, with pretty small amounts of HSA if amino acid compounds are present in sufficiently large amounts. However, this does not mean that in either case, the amount of one of the two components can be very small. For instance, it is necessary that the ratio of the combination stabilizer of this invention to urokinase is 10–50 mg of the sum of HSA and amino acid compounds to 6,000–60,000 international units (IU) of urokinase. The weight ratio of HSA to amino acid compounds as 1:0.05 to 1:10 preferably 1:0.1 to 1:4. When the amount of urokinase is greater or less than 6,000 IU, the sum of HSA and amino acid compounds should be increased or decreased within the above-noted range.

Of the various amino acid compounds usable in combination with HSA in this invention, those which exhibit the most powerful stabilizing effects are glutamic acid or the sodium salt thereof, threonine, arginine, the hydrochloric acid salt of arginine, histidine and the hydrochloric acid salt of histidine. In the case of threonine for example, when a combined stabilizer containing either 5 mg of threonine and 10 mg of HSA of 5 mg of HSA and 20 mg of threonine was used, urokinase showed a residual potency of 98% of the initial value in either case after having been stored for one month at 50° C. Of the amino acid compounds listed above, glutamic acid is especially effective so that the stabilizing effect of 10 mg of HSA is significantly increased by the addition of 1 mg of glutamic acid and becomes sufficiently high by the addition of 2 mg. Thus, glutamic acid is distinguished in the sense that it exhibits effectiveness even when present in small amounts.

Further, it was found quite unexpectedly that the glutamic acid-containing preparation of this invention has also an excellent characteristic property in thrombolytic activity. On evaluation of thrombolytic activity by the Chandler's loop method which is believed to reflect the thrombolytic activity in vivo in a most direct way among various experimental methods in vitro, it was found that the glutamic acid-containing preparation of this invention showed markedly higher thrombolytic activity compared with conventional preparations. This fact clearly pointed out how deep the clinical significance of this invention is.

The invention is explained below more clearly with reference to Experimental Examples. In the following examples, the activity of urokinase was assayed by the fibrinolytic method, and is expressed in terms of international units (IU).

EXPERIMENTAL EXAMPLE 1

Specific stabilizing effect shown by the combination stabilizer of this invention:

HSA was added to an aqueous solution of purified urokinase and diluted with a 0.025 M phosphate buffer solution of pH 7.0 to prepare a urokinase solution having a potency of 6,000 IU/ml and containing 10 mg/ml of HSA. To each 1 ml of the solution, were added respective amounts of additives such as amino acids. Each of the resulting solutions was lyophilized in a vial. In a similar manner to that described above, vials containing urokinase and 10 mg of HSA, 20 mg of mannit, 2 mg of glutamic acid, 10 mg of sodium glutamate or 10 mg of threonine were lyophilized. Further, a vial containing lyophilized purified urokinase alone was prepared. The lyophilized samples were stored in a thermostat at 50° C. and the stability of each sample was tested. The results obtained were as shown in Table 1.

TABLE 1

|  |  |  | Adjuvant | Residual potency after storing for 1 month at 50° C. (%) |
|---|---|---|---|---|
| This invention | HSA + polar amino acid | HSA (10 mg) | Glu (2 mg) | 96 |
|  |  |  | Glu-Na (10 mg) | 99 |
|  |  |  | Thr (10 mg) | 98 |
|  |  |  | His (10 mg) | 100 |
|  |  |  | Ser (10 mg) | 90 |
|  |  |  | Glu (NH$_2$) (10 mg) | 90 |
|  |  |  | Asp (4 mg) | 90 |
|  |  |  | Arg (10 mg) | 97 |
|  | HSA + non-polar amino acid | HSA (10 mg) | Cys (3 mg) | 67 |
|  |  |  | Leu (10 mg) | 70 |
|  |  |  | Met (10 mg) | 71 |
| Reference | Independent adjuvant |  | HSA (10 mg) | 72 |
|  |  |  | Mannit (20 mg) | 44 |
|  |  |  | Glu (2 mg) | 49 |
|  |  |  | Glu-Na (10 mg) | 70 |
|  |  |  | Thr (10 mg) | 51 |
|  | None added |  |  | 46 |

EXPERIMENTAL EXAMPLE 2

Optimum component ratio of the combination stabilizer of this invention:

In a manner similar to that in Experimental Example 1, lyophilized urokinase vials containing HSA and a polar amino acid in varied ratios were prepared. After having been stored at 50° C. for 1 month, each vial was tested for stability. The results obtained were as shown in Table 2.

TABLE 2

| Component ratio | | | Residual potency after storing for 1 month at 50° C. (%) |
|---|---|---|---|
| HSA content | Polar amino acid content | | |
| 40 mg | Glu | None | 80 |
|  |  | 2 mg | 92 |
|  |  | 8 mg | 96 |
| 10 mg | Glu | None | 72 |
|  |  | 1 mg | 92 |
|  |  | 2 mg | 96 |
|  |  | 3 mg | 98 |
|  |  | 5 mg | 98 |
| 5 mg | Glu | None | 72 |
|  |  | 1 mg | 90 |
|  |  | 2 mg | 94 |
|  |  | 3 mg | 98 |
|  |  | 5 mg | 98 |
| 10 mg | Glu-Na | None | 72 |
|  |  | 5 mg | 98 |
|  |  | 10 mg | 99 |
|  |  | 20 mg | 96 |
| 5 mg | Glu-Na | None | 72 |
|  |  | 5 mg | 96 |
|  |  | 10 mg | 98 |
|  |  | 20 mg | 98 |
| 10 mg | Thr | None | 72 |
|  |  | 5 mg | 98 |
|  |  | 10 mg | 98 |
|  |  | 20 mg | 98 |
| 5 mg | Thr | None | 72 |
|  |  | 5 mg | 96 |
|  |  | 10 mg | 98 |
|  |  | 20 mg | 98 |

EXPERIMENTAL EXAMPLE 3

Comparison of thrombolytic activity:

In order to predict the practical thrombolytic activity in vivo of the preparation of this invention, the thrombolytic activity was compared between the preparation of this invention and the conventional preparation by the Chandler's loop method according to Kitamura et al. (Note 1). The results obtained were as shown in Table 3. The preparation containing 10 mg of HSA and 2 mg of glutamic acid according to this invention showed a distinctly higher thrombolytic activity than that of a conventional preparation of the same urokinase potency of 6,000 IU/vial which contains no glutamic acid. The experiment was conducted by use of fresh rabbit blood. The amount of enzyme was adjusted by dilution in accordance with the assayed potency of each vial so that the final potency may become 150 IU/ml of blood.

TABLE 3

|  | Thrombolysis (%) (Note 3) |
|---|---|
| Glutamic acid containing preparation (Note 2) | 47.1 (Note 4) |
| Conventional preparation (Note 2) | 25.8 (Note 4) |

Note 1: Kitamura et al., "YAKKYOKU" (Practical Pharmacy), vol. 25, No. 10, p. 77 (1974)
Note 2: Both samples were prepared from the same purified urokinase solution. The potency and recipe of each vial were as follows: Glutamic acid-containing preparation: 6,000 IU/vial (containing 10 mg of HSA and 2 mg of glutamic acid) Conventional preparation: 6,000 IU/vial (containing 10 mg of HSA)
Note 3: Percent of thrombolysis with each sample was determined by referring to the weight of residual thrombii obtained by the addition of physiological saline in place of the enzyme solution.
Note 4: Average value of 15 samples.

Examples of the invention are shown below, but the invention is not limited thereto.

EXAMPLE 1

In about 1 ml of a 0.025 M phosphate buffer of pH 7.0, were dissolved 6,000 IU of urokinase, 10 mg of HSA, and 2 mg of glutamic acid. After bacterial filtration, the solution is filled in a vial and lyophilized to obtain a urokinase preparation for injection containing 10 mg of HSA and 2 mg of glutamic acid and having a potency of 6,000 IU.

EXAMPLE 2

In a similar manner to that in Example 1, a urokinase preparation for injection containing 10 mg of HSA and 10 mg of sodium glutamate and having a potency of 6,000 IU was obtained.

EXAMPLE 3

In a manner similar to that in Example 1, a urokinase preparation for injection containing 10 mg of HSA and 10 mg of histidine and having a potency of 6,000 IU was obtained.

EXAMPLE 4

In a manner similar to that in Example 1, a urokinase preparation for injection containing 10 mg of HSA and 10 mg of threonine and having a potency of 6,000 IU was obtained.

EXAMPLE 5

In a manner similar to that in Example 1, a urokinase preparation for injection containing 5 mg of HSA and 5 mg of threonine and having a potency of 6,000 IU was obtained.

EXAMPLE 6

In a manner similar to that in Example 1, a urokinase preparation for injection containing 10 mg of HSA and 2 mg of threonine and having a potency of 60,000 IU was obtained.

What is claimed is:

1. A method for preparing a stable urokinase composition suitable for injection into the human body by the lyophilization of urokinase which comprises lyophilizing an aqueous solution containing urokinase, human serum albumin and one or more amino acid compounds selected from the group consisting of glutamic acid, threonine, histidine, serine, glutamine, aspartic acid, arginine and salts thereof, said amino acid compound and human serum albumin being present in amounts effective to stabilize urokinase.

2. A method according to claim 1, wherein the amino acid compound is glutamic acid or sodium salt thereof, threonine, arginine or histidine.

3. A method for preparing a stable urokinase composition suitable for injection into the human body by the lyophilization of urokinase which comprises lyophilizing an aqueous solution containing urokinase, human serum albumin and glutamic acid, said glutamic acid and human serum albumin being present in amounts effective to stabilize urokinase.

4. A method according to claim 1, wherein the ratio of a mixture of human serum albumin and the amino acid compound to urokinase is 10–50 mg of the sum of human serum albumin and the amino acid compound to 6,000–60,000 IU of urokinase.

5. A method according to claim 4, wherein the weight ratio of human serum albumin to the amino acid compound is 1:0.05 to 1:10.

6. A method according to claim 5, wherein the weight ratio is 1:0.1 to 1:4.

7. A lyophilized urokinase composition comprising urokinase, human serum albumin, and one or more amino acid compounds selected from the group consisting of glutamic acid, threonine, histidine, serine, glutamine, aspartic acid, arginine and salts thereof, said amino acid compound and human serum albumin being present in amounts effective to stabilize urokinase.

8. A lyophilized urokinase composition according to claim 7, wherein the amino acid compound is glutamic acid or sodium salt thereof, threonine, arginine hydrochloric acid salt of arginine, histidine or hydrochloric acid salt of histidine.

9. A lyophilized urokinase composition comprising urokinase, human serum albumin and glutamic acid, said glutamic acid and human serum albumin being present in amounts effective to stabilize urokinase.

10. A lyophilized urokinase composition according to claim 7, wherein the ratio of human serum albumin and the amino acid compound to urokinase is 10–50 mg of the sum of human serum albumin and the amino acid compound to 6,000–60,000 IU of urokinase.

11. A lyophilized urokinase composition according to claim 7, wherein the weight ratio of human serum albumin to the amino acid compound is 1:0.05 to 1:10.

12. A lyophilized urokinase composition according to claim 11, wherein the weight ratio is 1:0.1 to 1:4.

* * * * *